(12) United States Patent
Worden et al.

(10) Patent No.: US 10,488,385 B2
(45) Date of Patent: Nov. 26, 2019

(54) WIRELESS SYSTEM AND METHOD FOR MEASURING AN OPERATIVE CONDITION OF A MACHINE

(71) Applicant: General Electric Company, Schenectady, NY (US)

(72) Inventors: Bret Dwayne Worden, Lawrence Park, PA (US); Mahalakshmi Shunmugham Balasubramaniam, Bangalore (IN); Ajith Kuttannair Kumar, Lawrence Park, PA (US); Jingjun Zhang, Lawrence Park, PA (US); Jennifer Lynn Coyne, Lawrence Park, PA (US); Sachidananda Chinagudi Jagadeesha, Bangalore (IN)

(73) Assignee: GE GLOBAL SOURCING LLC, Norwalk, CT (US)

( * ) Notice: Subject to any disclaimer, the term of this patent is extended or adjusted under 35 U.S.C. 154(b) by 72 days.

(21) Appl. No.: 15/678,403

(22) Filed: Aug. 16, 2017

(65) Prior Publication Data

US 2017/0363601 A1 Dec. 21, 2017

Related U.S. Application Data

(63) Continuation of application No. 14/421,245, filed as application No. PCT/US2013/055983 on Aug. 21, 2013, now Pat. No. 9,746,452.

(Continued)

(51) Int. Cl.
*G01N 33/26* (2006.01)
*F16N 29/00* (2006.01)
*G01M 13/02* (2019.01)

(52) U.S. Cl.
CPC ............. *G01N 33/26* (2013.01); *F16N 29/00* (2013.01); *G01M 13/02* (2013.01)

(58) Field of Classification Search
CPC ......... G01N 33/26; F16N 29/00; G01M 13/02
(Continued)

(56) References Cited

U.S. PATENT DOCUMENTS 3,623,684 A 11/1971 Kline
6,457,564 B1 10/2002 Damm et al.
(Continued)

FOREIGN PATENT DOCUMENTS

JP H05-52397 U 7/1993
JP 2005-345277 A 12/2005
(Continued)

OTHER PUBLICATIONS

Machine Translation and Notification of Reasons for Refusal issued in connection with corresponding JP Application No. 2015-528619 dated Jul. 4, 2017.
(Continued)

*Primary Examiner* — Nathaniel J Kolb
(74) *Attorney, Agent, or Firm* — Joseph L. Hoffmann; The Small Patent Law Group LLC

(57) ABSTRACT

A system includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system also includes a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

18 Claims, 9 Drawing Sheets

Related U.S. Application Data

(60) Provisional application No. 61/692,230, filed on Aug. 22, 2012.

(58) Field of Classification Search
USPC .................. 73/290 R–334, 290 B, 290 V
See application file for complete search history.

(56) References Cited

U.S. PATENT DOCUMENTS

| | | | | |
|---|---|---|---|---|
| 7,814,786 | B2* | 10/2010 | Woodard | G01R 33/1223 73/291 |
| 8,215,166 | B2* | 7/2012 | Cunningham | G01F 23/268 73/304 C |
| 8,542,023 | B2 | 9/2013 | Potyrailo et al. | |
| 8,542,024 | B2 | 9/2013 | Potyrailo et al. | |
| 9,195,925 | B2 | 11/2015 | Potyrailo et al. | |
| 9,538,657 | B2 | 1/2017 | Potyrailo et al. | |
| 9,589,686 | B2 | 3/2017 | Potyrailo et al. | |
| 2002/0105429 | A1* | 8/2002 | Donner | B61K 9/04 340/682 |
| 2005/0007239 | A1* | 1/2005 | Woodard | B60C 23/0449 340/10.2 |
| 2008/0184795 | A1* | 8/2008 | Woodard | G01R 33/1223 73/304 C |
| 2009/0139325 | A1* | 6/2009 | Cunningham | E03F 5/16 73/304 C |
| 2010/0154534 | A1* | 6/2010 | Hampton | G01F 23/265 73/304 C |
| 2010/0200082 | A1* | 8/2010 | Mantua | G01F 23/703 137/409 |
| 2011/0166812 | A1* | 7/2011 | Potyrailo | G01D 9/005 702/65 |
| 2011/0320142 | A1 | 12/2011 | Surman et al. | |
| 2012/0116683 | A1* | 5/2012 | Potyrailo | G01N 27/02 702/19 |
| 2012/0158321 | A1* | 6/2012 | Bommer | G01F 23/0084 702/55 |
| 2012/0166095 | A1 | 6/2012 | Potyrailo et al. | |
| 2013/0068015 | A1* | 3/2013 | Sinha | G01F 23/263 73/304 C |
| 2014/0182363 | A1 | 7/2014 | Potyrailo et al. | |
| 2016/0018382 | A1 | 1/2016 | Worden et al. | |

FOREIGN PATENT DOCUMENTS

| | | |
|---|---|---|
| JP | 2007-131157 A | 5/2007 |
| JP | 2007-256033 A | 10/2007 |

OTHER PUBLICATIONS

Machine Translation and Decision to Grant issued in connection with corresponding JP Application No. 2015-528619 dated Oct. 31, 2017.

* cited by examiner

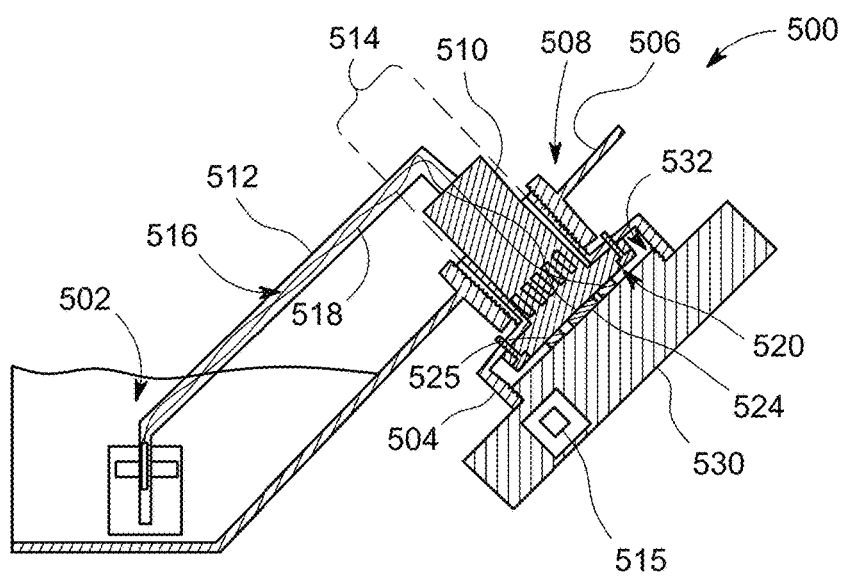
FIG. 11
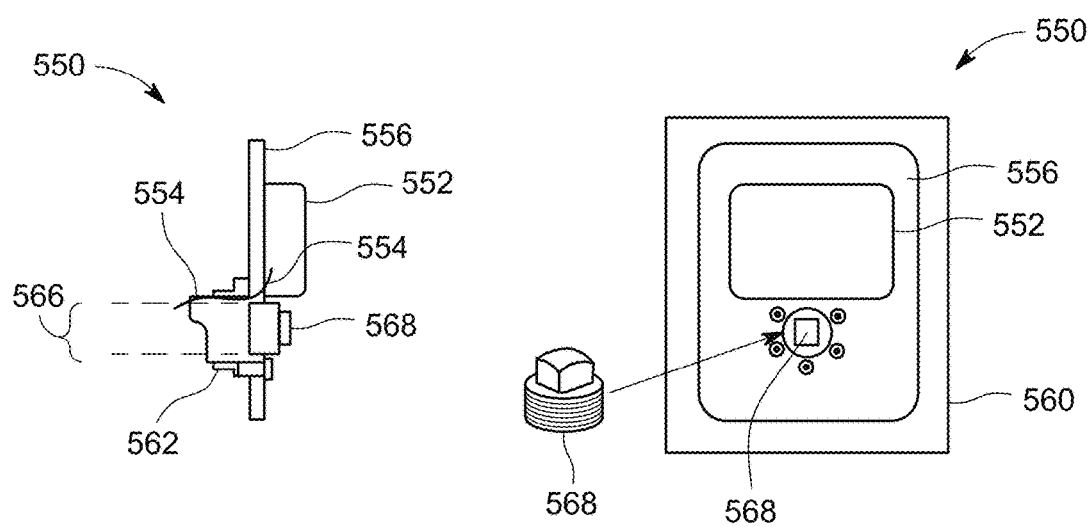
FIG. 12
FIG. 13

WIRELESS SYSTEM AND METHOD FOR MEASURING AN OPERATIVE CONDITION OF A MACHINE

CROSS-REFERENCE TO RELATED APPLICATIONS

This application is a continuation of and claims priority to U.S. patent application Ser. No. 14/421,245, which was filed 12 Feb. 2015, and which claims the benefit of U.S. Provisional Patent Application No. 61/692,230, which was filed 22 Aug. 2012. The entire disclosures of these applications are incorporated herein by reference.

FIELD

One or more embodiments of the subject matter described herein generally relate to systems and methods for detecting an operative condition of a machine or a component of the machine that has movable parts.

BACKGROUND

Many industrial machines (e.g., locomotives, trucks, earth-moving equipment, windmills, and the like) include elements or assemblies (e.g., mechanical drive trains) that operate within difficult environments and/or endure substantial amounts of thermal or torsional stress as well as shock and vibration. It is often desirable to monitor a condition of an element or assembly so that it may be replaced or repaired before severe and permanent damage is sustained by the machine. Often, fluid lubricants are used to provide lubrication and cooling to increase performance of the machine and/or to increase the lifetime operation of the machine. Lubricants reduce the friction between two parts that engage each other and may also dissipate heat that is generated by the friction between the two parts. As one specific example, speed control from a traction motor or other provider of mechanical power may be accomplished with a gear train or drive train. Gear trains typically include at least two gears that engage each other. For instance, teeth of a first gear (e.g., pinion gear) may engage teeth of a larger gear at a gear mesh. It is common for the gears to be lubricated by a lubricant (e.g., oil) to reduce the friction between the gears and to facilitate the dissipation of heat that is generated during operation. For the gears to be suitably lubricated, a designated amount of lubricant is available for use by the gears.

A gear train may include a gear case that surrounds one or more parts of the gear train. The gear case has a reservoir for holding the lubricant. At least one of the gears may move through the reservoir to lubricate the gear and consequently the gear mesh. At least one of the gears may be coupled to a shaft that projects out of the gear case. To prevent leakage from the reservoir or the gear case, the interface between the shaft(s) and the gear case is sealed.

The sealed interfaces, however, are often exposed to harsh conditions. For example, gear trains of locomotives are frequently exposed to large differences in temperature, humid environments, dry environments, abrasive dirt or grime, and/or challenging vibratory states. These conditions may cause a failure in the sealed interface thereby resulting in leakage of the lubricant. When an insufficient supply of lubricant is available for the gears, the machine may be susceptible to gear train or rolling element bearing damage that results in a locked axle condition. In the case of locomotives, locked axles may require the locomotive to be removed from service and sent to a facility for repair. Both the removal and repair of the locomotive may be time-consuming and costly. Furthermore, the lost productivity of the locomotive is also costly.

In addition to having a sufficient amount of lubricant, it is also desirable for the lubricant to have a sufficient quality during operation. For example, lubricants in a reservoir can become contaminated by water, metallic particles, and non-metallic particles. Contaminated fluids may lead to damaged parts or a decreased performance of the machine. In addition, the lubricant may age due to repetitive thermal and viscous cycles resulting in the loss of fluid properties such as viscosity.

Conventional methods of inspecting fluids of a machine include visual inspection of the fluid (e.g., dipsticks) or a sensor that is directly wired to a system. However, these methods may not be practical and/or may have limited capabilities. For example, due to the configuration of some machines, it may be difficult to visually inspect the fluid. Also, hardwired sensors may not be suitable for machines that frequently move and/or are exposed to harsh conditions.

In addition to detecting the quantity and/or the quality of a liquid used by a machine, it may be desirable to obtain other information regarding an operative condition of a machine. For example, when an industrial machine is operating properly, the machine may have known or expected vibratory states. However, when a part of the machine is damaged or otherwise not operating properly, the vibrations of the machine may change. Therefore, it may be desirable to detect the vibrations of certain elements in a machine to monitor a health of the elements, other components of the machine, or the machine overall.

BRIEF DESCRIPTION

In accordance with an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

While multiple embodiments are disclosed, still other embodiments of the described subject matter will become apparent from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 11 is a cross-section of a wireless device utilizing the sensor of FIG. 5 in accordance with an embodiment.

FIG. 12 is a cross-section of a portion of a wireless device formed in accordance with an embodiment.

FIG. 13 is a front view of the wireless device of FIG. 13.

DETAILED DESCRIPTION

Figure 1:
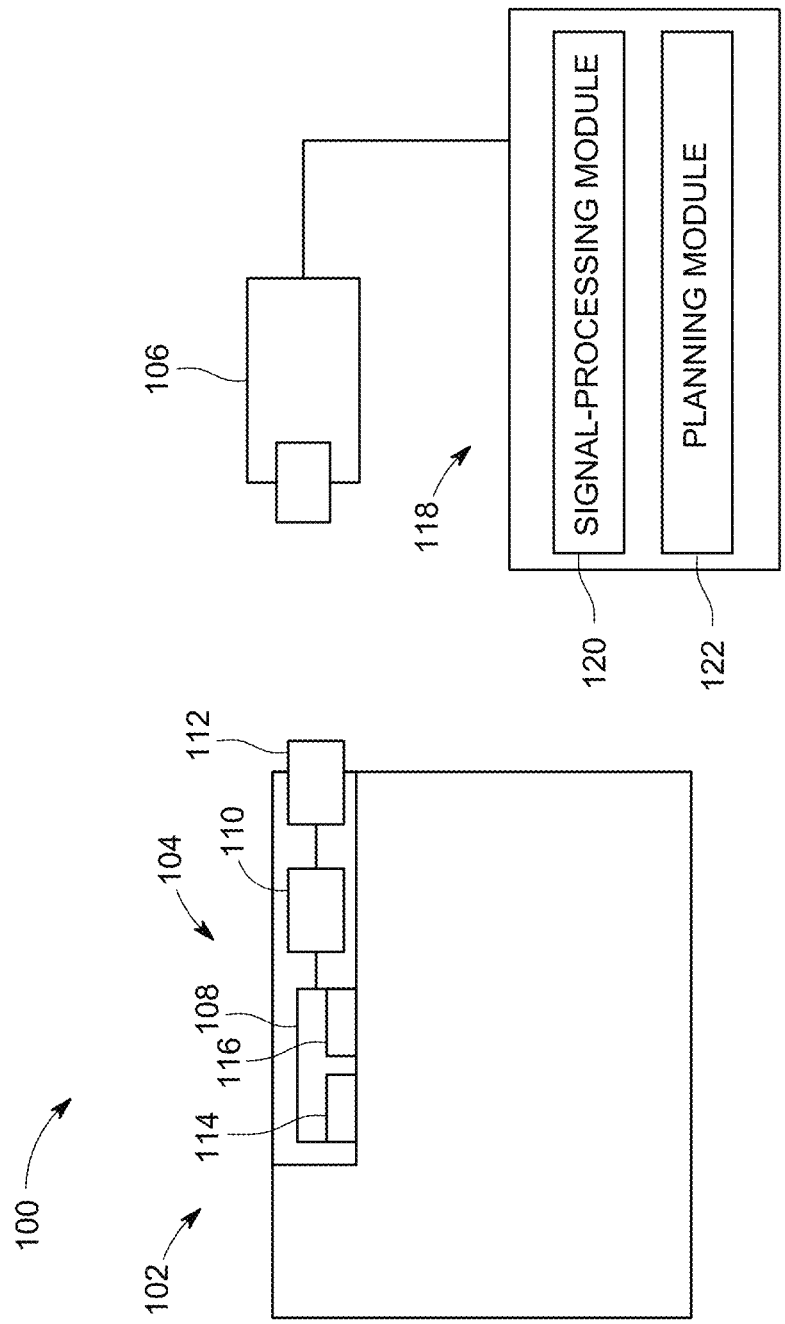
FIG. 1 is a schematic view of a system in accordance with an embodiment.

Embodiments described herein include various systems, assemblies, devices, apparatuses, and methods that may be used in a connection with obtaining one or more measurements of a machine. The measurement(s) may be representative or indicative of an operative condition of the machine. As used herein, an "operative condition of the machine" may refer to an operative condition of the machine as a whole or an operative condition of a component (e.g., element, assembly, or sub-system) of the machine. As used herein, the term "operative condition" relates to a present state or ability of the component and/or a future state or ability. For example, the measurement may indicate that a component is not functioning in a sufficient manner, is damaged, is likely to be damaged if it continues to operate in a designated manner, is not likely to perform appropriately under designated circumstances, and/or is likely to cause damage to other components of the machine.

As an example with respect to locomotives or other rail vehicles, one or more measurements obtained from a locomotive or other rail vehicle may indicate that a lubricant in the component (e.g., drive train, gearbox, engine, and the like) is low or has an insufficient quality. Embodiments set forth herein may generate an operating plan that is based on the measurement(s). For instance, the operating plan may include instructions to disable an axle or to limit tractive and/or braking efforts of the axle. The operating plan may indicate which element of the gearbox should be replaced and/or how the machine is to be operated until the gearbox is replaced. Such operating plans are described in greater detail below.

The measurement may be one of a plurality of measurements that are analyzed according to embodiments described herein. For instance, embodiments may comprise analyzing multiple measurements that were obtained at different times from a single sensor to determine an operative condition of the machine. By way of example, a series of measurements from a single sensor in a gear case may indicate that a lubricant level has substantially changed and, thus, the gear case is leaking. Embodiments may also comprise analyzing measurements from a plurality of sensors of the same type. For example, machines may include multiple gearboxes. Vibration measurements from the gearboxes may indicate that one of the gearboxes is operating differently than the others and, thus, may be damaged or in need of maintenance. Embodiments may also comprise analyzing different types of measurements to determine an operative condition of the machine. For example, the vibration measurements may be analyzed in light of the speed at which the gears are driven and/or current environmental conditions. Additional measurements or factors are set forth below.

The measurements may be wirelessly transmitted from a device to a reader, which may also be referred to as a receiver. For example, radio waves representative of the measurement(s) may be transmitted from a transmitter (e.g., antenna) of the wireless device to a remote reader. The reader may be a handheld reader (e.g., capable of being carried in a single hand by a technician) or an otherwise movable reader. In some embodiments, the reader may have a fixed position. For example, for embodiments in which the machine is a vehicle, the reader may have a stationary position along a designated path that is traversed by the vehicle (e.g., railroad tracks, weighing stations, tollbooths). When a vehicle passes the reader, the reader may interrogate one or more wireless devices to obtain measurements. Remote readers may also be located on-board the vehicle. For example, a locomotive or other rail vehicle may have a control system that receives data from multiple sources, including one or more wireless devices that communicate the measurements to the control system.

The measurement may be detected or obtained by a sensor when the device having the sensor is interrogated by the reader. Alternatively or additionally, the sensor may obtain data at designated intervals (e.g., one measurement/hour, one measurement/minute, and the like) and/or when a designated event occurs. For example, measurements may only be obtained after the vehicle has been interrogated or after the vehicle has remained stationary for a certain amount of time (e.g., ten minutes). In some embodiments, the wireless device includes a storage unit (e.g., memory) where multiple measurements may be stored or logged. The wireless devices may also include a power source that is integral to the device. Examples of electrical power sources include batteries and energy harvesting devices. Energy harvesting devices convert energy in the surrounding environment, such as kinetic energy (e.g., vibrations), thermal energy, and electromagnetic energy. In particular embodiments, the wireless devices may include or be coupled to a vibratory energy harvesting device that converts kinetic energy into electrical energy.

The foregoing description of certain embodiments of the present inventive subject matter will be better understood when read in conjunction with the appended drawings. To the extent the figures illustrate diagrams of the functional blocks of various embodiments, the functional blocks are not necessarily indicative of the division between hardware and circuit. Thus, for example, one or more of the functional blocks (for example, controllers or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

FIG. 1 is a schematic diagram of a system 100 formed in accordance with one embodiment. The system 100 is configured to obtain one or more measurements that are representative of an operative condition of a machine 102 or a component of the machine 102 (e.g., element, assembly, or sub-system of the machine 102). By way of example only, the machine 102 may be a motive machine or vehicle, such as an off-highway vehicle (e.g., vehicles that are not designed or allowed by law or regulation to travel on public roads, highways, and the like). Off-highway vehicles include locomotives, mining vehicles, construction equipment, agricultural equipment, industrial equipment, marine vessels, and the like. In some cases, the vehicle may be part of a vehicle consist in which multiple vehicles are linked directly or indirectly to one another in a common vehicle system (e.g., train). In some embodiments, the machine is an automobile. In other embodiments, the machine is not configured to travel. For example, the machine may be a windmill or a power-generating turbine.

The operative condition may relate to a health or status of a designated component of the machine. Non-limiting examples of such components include a gearbox, a gear case, an air compressor, a turbo-charger, or a drive train. The measurement may be analyzed to determine, for example, that a component is damaged, is operating improperly (e.g., insufficiently or not at all), and/or is operating in a manner that will lead to or cause greater damage to the component or other component of the machine 102.

In particular embodiments, the operative condition is determined based on an amount or quality of liquid used by the machine 102 and/or a vibratory state of the machine 102. For instance, in some embodiments, the component may be a gear case that has a reservoir for storing a lubricant liquid. A low level or quantity of the liquid in the reservoir may indicate that the gear case is damaged. In particular, a low level or quantity may indicate that the gear case is leaking the liquid. In other embodiments, a component may have a particular vibratory state(s) when the component is operating properly. For example, a mechanical element may be configured to oscillate in a known or expected manner during operation. However, if the mechanical element is damaged or operating improperly, the mechanical element may have a different vibratory state.

As shown, the system 100 may include a wireless device 104 that is configured to wirelessly communicate data signals to a remote reader 106. The data signals may represent the measurement(s) obtained by the wireless device 104. To this end, the wireless device 104 may include a sensor 108, a processing unit 110, and a transmitter 112. The sensor 108 is configured to measure an operating parameter of the machine 102 and thereby obtain a measurement. In some embodiments, the sensor 108 includes a detector or transducer 114 and an activator 116. The activator 116 may be configured to provide a stimulus (e.g., sound waves, light, electric current, etc.) that causes a response by a component-of-interest or is affected by the component-of-interest. The detector 114 may be configured to detect the response that is caused by the stimulus or the affect that the component-of-interest has on the stimulus. For example, the stimulus may be sound waves that are detected to determine a liquid level (e.g., sonar). The stimulus may be light signals that are projected by a laser into a liquid to determine how much of the light signals are absorbed by the liquid. Another stimulus may be electric current. In other embodiments, the sensor 108 does not include an activator 116. Instead, the detector 114 may detect sound, vibrations, light, temperature, electrical properties, or other properties that occur in the environment without a stimulus provided by an activator.

The processing unit 110 is operably coupled to the sensor 108. The processing unit 110 is configured to receive measurement signals from the sensor 108 and process the measurement signals to provide data signals. The processing unit 110 may be an analog-to-digital converter (ADC). Alternatively or in addition to the ADC, the processing unit 110 may include a logic-based device that transforms the measurement signals into data signals. The data signals may then be configured to be transmitted to the reader 106 by the transmitter 112. For example, the processing unit 110 may be a computer processor, controller (e.g., microcontroller) or other logic-based device that performs operations based on one or more sets of instructions (e.g., software). The instructions on which the processing unit 110 operates may be stored on a tangible and non-transitory (e.g., not a transient signal) computer readable storage medium, such as a memory. The memory may include one or more types of memory, such as hard drives, flash drives, RAM, ROM, EEPROM, and the like. Alternatively, one or more of the sets of instructions that direct operations of the processing unit 110 may be hard-wired into the logic of the processing unit 110, such as by being hard-wired logic formed in the hardware of the processing unit 110.

The transmitter 112 is operably coupled to the processing unit 110 and is configured to wirelessly communicate the data signals to the reader 106. In some embodiments, the transmitter 112 is a transceiver that is configured to transmit the data signals and receive other signals, such as interrogation signals from the reader 106.

In some embodiments, the sensor 108, the processing unit 110, and the transmitter 112 are localized within and/or attached directly to the machine such that the sensor 108, the processing unit 110, and the transmitter 112 are proximate to each other and form a single device. The sensor 108, the processing unit 110, and the transmitter 112 may be in a localized spatial region of the machine that is separate from a computing system that controls operation of the machine. For example, the processing unit 110 and the transmitter 112 may be integrated with the same component such that the processing unit 110 and the transmitter 112 have fixed positions with each other. More specifically, the processing unit 110 and the transmitter 112 may be at least partially integrated onto a common component (e.g., circuit board) and/or positioned within a common container or housing that is coupled to the machine. The common container may not be coextensive with the machine and, instead, may be a separate component that is attached to or disposed within the machine-of-interest. By way of example only, some or all the components of the processing unit 110 and the transmitter 112 may be located within 50 cm of each other, 20 cm of each other, 10 cm of each other or, more particularly, within 5 cm of each other.

In some embodiments, the processing unit 110 and the transmitter 112 may be part of a common RFID unit (e.g., tag, chip, card, and the like). Optionally, the sensor 108 may also be part of the common RFID unit. In other cases, the sensor 108 is separate from, but operably coupled to, the RFID unit and is only a short distance from the RFID unit. For example, the sensor 108 may be located within 50 cm or less of the RFID unit and communicatively coupled via wires or wireless communication. The RFID unit may be formed in accordance with RFID technology, which may include integrated circuit technology. For example, the RFID unit may be an electronic circuit that is capable of wireless communication. In some instances, the RFID unit may satisfy one or more established RFID standards and/or guidelines, such as standards and guidelines formed by the International Organization for Standardization (ISO), the International Electrotechnical Commission (IEC), ASTM International, the DASH7 Alliance, EPCglobal, the Financial Services Technology Consortium (FSTC).

In certain embodiments, the wireless device 104 is not physically electrically connected (e.g., not connected by wires or other conductors) to any of the one or more computers or other controller-based units in the machine. For example, in the context of trains, the wireless device 104 may be partially disposed within a reservoir and/or attached to a wall that defines the reservoir and is not physically electrically connected to the computing system that controls operation of the train. In such embodiments, the data signals from the wireless device 104 may be wirelessly transmitted from the wireless device 104 to, for example, a reader that is on-board or off-board. More specifically, the data signals may not be transmitted via wire/cables or other physical electrical connections. In one or more embodiments, at least portions of the processing unit 110 and the transmitter 112 may be directly connected to a wall that defines the reservoir (e.g., a wall that bears a pressure of and/or contacts the liquid in the reservoir) and/or to a structure immediately connected to the wall (e.g., support structure of the reservoir, gear case, or the like).

Various forms of wireless communication may be transmitted and received by the wireless device 104. For example, the transmitter 112 may be configured to receive and/or transmit radio signals, optical signals, signals based on sound, or signals based on magnetic or electric fields. In particular embodiments, the transmitter 112 is configured to receive and/or transmit radio signals in one or more radio frequencies. The wireless signals may be transmitted along a narrow radio band. In narrow band transmission, a single carrier frequency is used. Alternatively, the wireless signals may be transmitted within a spectrum of radio frequencies. For example, in spread spectrum transmission, the signals may be transmitted over a number of different radio frequencies within a radio band. The data signals may be modulated for transmission in accordance with any one of a number of modulation standards, such as frequency-hopping spread spectrum (FHSS), direct-sequence spread spectrum (DSSS), or chirp spread spectrum (CSS).

One wireless communication standard that may be used by embodiments described herein is IEEE 802.15.4. The IEEE 802.15.4 standard may operate within one of three frequency bands: (1) 868.0-868.6 MHz; (2) 902-928 MHz; or (3) 2400-2483.5 MHz. A number of channels may be used in each of the frequency bands. Embodiments may also use frequency bands that are associated with RFID technology, such as 120-150 kHz, 13.56 MHz, 865-868 MHz, 902-028 MHz, 2450-5800 MHz, or 3.1-10 GHz. Ultra wideband (UWB) may also be used.

In some embodiments, a transmission range of the data signals and/or the signals from the reader 106 is about 0-10 meters or from about 0-20 meters. In other embodiments, the transmission range may be greater, such as up to 100 meters or more.

Various embodiments may be based on or consistent with radio frequency identification (RFID) technology. For example, the wireless device 104 may be a passive sensor, a semi-passive sensor, or an active sensor. A passive sensor may not include a power source. Instead, the power may be based on inductive coupling or backscatter coupling with the reader. A semi-passive sensor may include a power source for only designated functions. For example, a battery and/or an energy harvesting device may be used to increase the transmission distance. The passive and semi-passive sensors may be particularly suitable for when the reader is present (e.g., within transmission range so that the sensors can be powered by the reader). An active sensor may include a power source for powering multiple functions (e.g., detection, reception, and transmission). Active sensors may be used in embodiments in which the reader is configured to only receive data signals and not transmit interrogation signals.

The reader 106 may be operably connected to a control system 118 having a signal-processing or diagnostic module 120 and, optionally, a planning module 122. Like the processing unit 110, the modules 120, 122 may be a computer processor, controller (e.g., microcontroller), or other logic-based device that performs operations based on one or more sets of instructions. The instructions on which the modules 120, 122 operates may be stored on a tangible and non-transitory (e.g., not a transient signal) computer readable storage medium, such as a memory. Alternatively, one or more of the sets of instructions that direct operations of the modules 120, 122 may be hard-wired into the logic of the modules 120, 122. The module 120, 122 may be located on separate devices (e.g., separate processors) or may be located on common processor.

The signal-processing module 120 may be configured to determine, based on the data signals received by the reader 106, whether the machine 102 is operating improperly. The signal-processing module 120 may determine whether the machine 102 is operating properly or improperly by analyzing the data signals that are representative of the measurements. For example, the signal-processing module 120 may use a look-up table or other databases that provides acceptable ranges of operation. If the measurement based on the data signals is not within the range, the signal-processing module 120 may determine that the machine 102 is not operating properly. In some cases, based on the measurement(s), the signal-processing module 120 may be able to determine whether a particular component of the machine 102 needs maintenance, repair, or replacement or whether the machine 102 requires an overhaul of a sub-system.

Based on the measurement(s), the signal-processing module 120 may request that an operating plan be generated by the planning module 122. The operating plan may be configured to improve the performance of the machine 102 and/or to limit the performance of the machine 102 to prevent damage or additional damage. The operating plan may include instructions for replacing, maintaining, modifying, and/or repairing a designated component or components of the machine 102.

The operating plan may be based on the operative condition, which is at least partially a function of the measurement(s) obtained. For instance, if a capacitive measurement indicates that the liquid level is less than sufficient, but a substantial amount remains in the gear case, then the operating plan may include instructions for refilling the liquid at a first facility and then resealing the gear case at a second facility located further away. However, if a capacitive measurement indicates that the liquid level quickly reduced to little or no measurable amount of liquid, then the operating plan may instruct that the gear case be replaced at a designated facility.

In the context of a locomotive or other vehicle, the operating plan may include instructions for controlling tractive and/or braking efforts of the vehicle. In particular, the operating plan may be partially based on the measurements of the operative condition of the machine. The instructions may be expressed as a function of time and/or distance of a trip along a route. In some embodiments, travel according to the instructions of the operating plan may cause the vehicle to reduce a stress on a component-of-interest of the machine than the component would typically sustain during normal operation. For example, the operating plan may instruct the vehicle to reduce horsepower delivered to an axle, to intermittently drive the axle, or to disable the axle altogether. The vehicle may be autonomously controlled according to the operating plan or the instructions of the operating plan may be presented to an operator of the vehicle so that the operator can manually control the vehicle according to the operating plan (also referred to herein as a "coaching mode" of the vehicle).

In some embodiments, the operating plan that is generated when it is determined that the machine is operating improperly is a "revised" operating plan that supersedes or replaces another operating plan. More specifically, due to the newly acquired measurements, the control system may determine that the currently-implemented operating plan should be modified and, as such, may generate a revised operating plan to replace the other.

Operating plans may be optimized to achieve designated goals or parameters. As used herein, the term "optimize" (and forms thereof) are not intended to require maximizing or minimizing a characteristic, parameter, or other object in all embodiments described herein. Instead, "optimize" and its forms may include increasing or decreasing (as appropriate) a characteristic, parameter, or other object toward a designated or desired amount while also satisfying other conditions. For example, optimized stress levels on a component may not be limited to a complete absence of stress or that the absolute minimum amount of stress. Rather, optimizing the stress level may mean that the stress is controlled, while also satisfying other conditions (e.g., speed limits, trip duration, arrival time). For example, the stress sustained by a component may be controlled so that the vehicle may arrive at its destination without the component being severely damaged.

The planning module 122 is configured to use at least one of vehicle data, route data (or a route database), part data, or trip data to generate the operating plan. The vehicle data may include information on the characteristics of the vehicle. For example, when the vehicle system is a rail vehicle, the vehicle data may include a number of rail cars, number of locomotives, information relating to an individual locomotive or a consist of locomotives (e.g., model or type of locomotive, weight, power description, performance of locomotive traction transmission, consumption of engine fuel as a function of output power (or fuel efficiency), cooling characteristics), load of a rail vehicle with effective drag coefficients, vehicle-handling rules (e.g., tractive effort ramp rates, maximum braking effort ramp rates), content of rail cars, lower and/or upper limits on power (throttle) settings, etc.

Route data may include information on the route, such as information relating to the geography or topography of various segments along the route (e.g., effective track grade and curvature), speed limits for designated segments of a route, maximum cumulative and/or instantaneous emissions for a designated segment of the route, locations of intersections (e.g., railroad crossings), locations of certain track features (e.g., crests, sags, curves, and super-elevations), locations of mileposts, and locations of grade changes, sidings, depot yards, and fuel stations. The route data, where appropriate, may be a function of distance or correspond to a designated distance of the route.

Part data may include, for example, historical data or proprietary data regarding the lifetime operability of a component. The data may include baseline data for a designated speed and/or load on the machine. Additional factors may be part of the baseline data. For example, if the lubricant has a designated quantity in the gear case, the part data may include data from identical components that operated with an approximately equal lubricant level. The data may include how long the component is capable of operating at a designated speed.

Trip data may include information relating to a designated mission or trip, such as start and end times of the trip, start and end locations, route data that pertains to the designated route (e.g., effective track grade and curvature as function of milepost, speed limits), upper cumulative and/or instantaneous limits on emissions for the trip, fuel consumption permitted for the trip, historical trip data (e.g., how much fuel was used in a previous trip along the designated route), desired trip time or duration, crew (user and/or operator) identification, crew shift expiration time, lower and/or upper limits on power (throttle) settings for designated segments, etc. In one embodiment, the planning module 122 includes a software application or system such as the Trip Optimizer™ system developed by General Electric Company.

Figure 2:
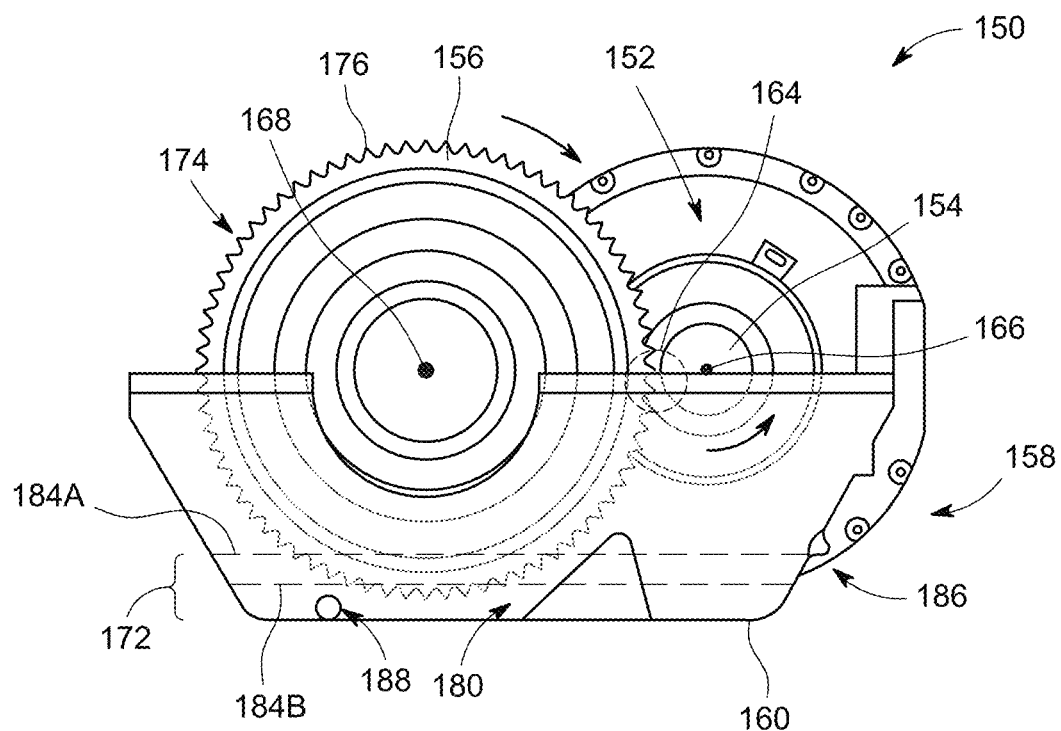
FIG. 2 is a side view of a drive train in accordance with an embodiment.
Figure 3:
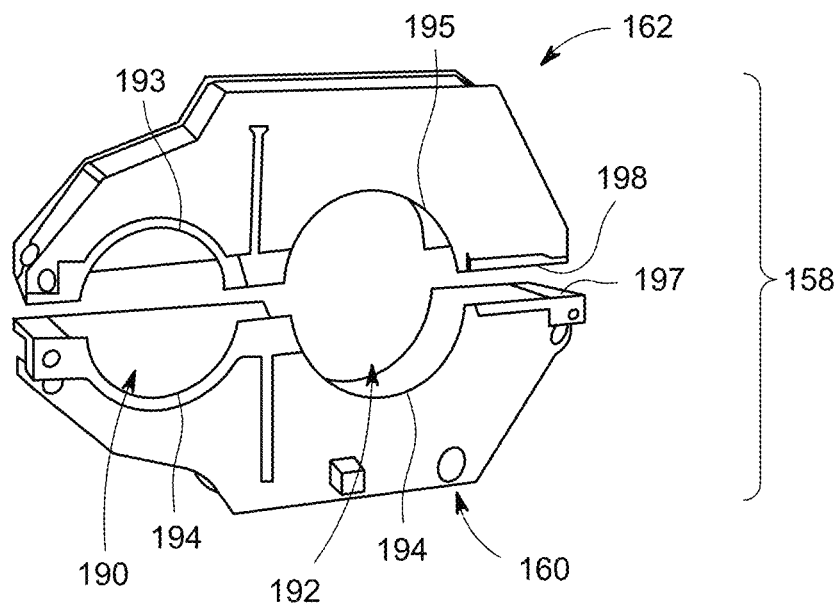
FIG. 3 is a partially exploded view of a gear case that may be used by the drive train of FIG. 2.

FIG. 2 is a side view of a drive train (or final drive) 150 in accordance with one embodiment. The drive train 150 includes a traction motor 152, a first (or pinion) gear 154, a second gear 156, and a base portion or shell 160 of a gear case 158. A top portion or shell 162 of the gear case 158 is shown in FIG. 3. As shown in FIG. 2, the first gear 154 and the second gear 156 engage each other at a gear mesh 164.

During operation of the drive train 150 the traction motor 152 drives the first gear 154 by rotating an axle (not shown) coupled to the first gear 154 about an axis of rotation 166. The first gear 154 may be rotated, for example, in a counter-clockwise direction as viewed in FIG. 2. Due to the engagement at the gear mesh 164, the first gear 154 rotates the second gear 156 in a clockwise direction about an axis of rotation 168. The second gear 156 is coupled to an axle (not shown) that rotates with the second gear 156. The axle of the second gear 156 is coupled to wheels (not shown) that are rotated with the axle. The wheels engage a surface (e.g., rails or tracks) to move the machine.

The gear case 158 includes a reservoir 172 that is configured to hold a lubricant liquid 180 (e.g., oil). The gear case 158 has a fill or inlet port 186 and a drain or outlet port 188. The liquid 180 may be provided to the reservoir 172 through the fill port 186 and drained through the drain port 188.

As shown in FIG. 2, the second gear 156 has teeth 176 along an edge 174 of the second gear 156. When the liquid 180 is held within the gear case 158, the liquid 180 may have a fill level 184. FIG. 2 illustrates a first fill level 184A and a second fill level 184B. The second fill level 184B is lower than the first fill level 184A. In some embodiments, when the drive train 150 is operating properly, the quantity of the liquid 180 correlates to the first fill level 184A such that the edge 174 of the second gear 156 is sufficiently submerged within or bathed by the liquid 180. However, when the fill level is lowered to, for example, the fill level 184B, the edge 174 and teeth 176 may be insufficiently lubricated. Such circumstances may occur when the gear case 158 has a leak.

FIG. 3 is a partially exploded view of the gear case 158 and illustrates the base and top portions 160, 162 before the base and top portions 160, 162 are coupled to the drive train to surround the first and second gears 154, 156. As shown, the gear case 158 may include first and second gear-receiving openings 190, 192 that are sized to receive the first and second gears 154, 156 (FIG. 2), respectively. The gear-receiving openings 190, 192 may be defined by opening edges 193-196 and the base and top portions 160, 162 may engage each other along case edges 197, 198.

When the drive train 150 is fully constructed and operational, the opening edges 193-196 engage the portions of the drive train 150 along sealable interfaces. The case edges 197, 198 may also be coupled to each other along a sealable interface. During operation of the drive train 150, however, the interfaces may become damaged or worn such that the interfaces are no longer sufficiently sealed. For example, when the drive train 150 is part of a locomotive, the opening edges 193-196 or the case edges 197, 198 may become worn, damaged, or separated such that the liquid 180 is permitted to escape the reservoir 172. Accordingly, the amount of liquid 180 may reduce such that the fill level 184 (FIG. 2) lowers.

Embodiments described herein may be configured to detect that the amount of liquid 180 has reduced. In addition, due to the wear, damage, or separation of the base and top portions 160, 162, the gear case 158 (or portions thereof) may exhibit different vibratory characteristics. For example, a gear case that is sufficiently sealed with respect to the drive train 150 and has a sufficient fill level 184 may exhibit a first vibratory state when the drive train 150 is driven at a first speed. However, a gear case that is insufficiently sealed with respect to the drive train 150 and/or has an insufficient fill level 184 may exhibit a second vibratory state that is different than the first vibratory state when the drive train 150 is driven at the first speed. Embodiments described herein may be configured to detect and measure the different vibratory states. In certain embodiments, a wireless device, such as those described herein, is at least partially disposed within the reservoir 172 and/or directly attached to a portion of the gear case 158. For example, at least a portion of the wireless device 158 may be directly secured or affixed to a wall of the gear case 158, such as the wall that defines the reservoir 172. In some embodiments, the wireless device 172 is not physically electrically connected to other components of the machine, such as a computing system that controls operation of the machine.

In addition to liquid level and vibrations, embodiments may be configured to detect other characteristics. For example, other measurements may relate to a quality (e.g., degree of contamination) of the liquid. Contaminants may include water, metallic particles, and/or non-metallic particles. Furthermore, embodiments are not limited to the drive train or a gear case of the driver train. For example, measurements that may be obtained for a drive train may also be obtained for a turbo-charger, an air compressor, an engine, and the like. Other components of a machine may also be measured by wireless devices described herein.

Figure 4:
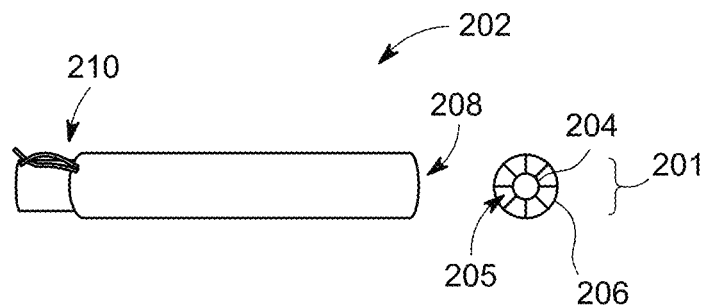
FIG. 4 is a side view of a capacitive-type sensor in accordance with an embodiment.
Figure 5:
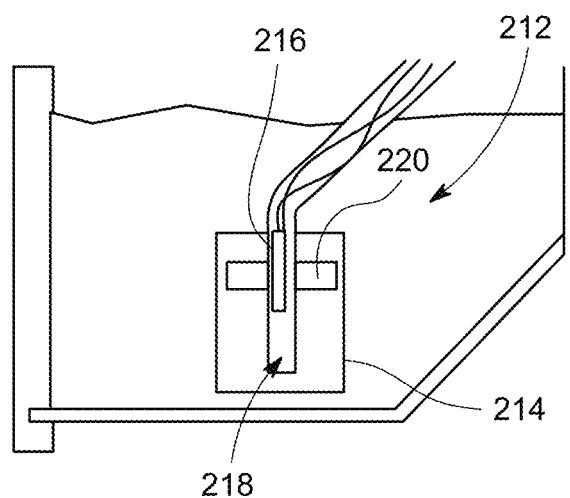
FIG. 5 is a schematic view of a magnetic float/reed switch sensor in accordance with an embodiment.
Figure 6:
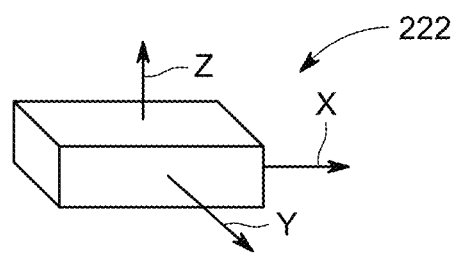
FIG. 6 is a schematic view of an accelerometer in accordance with an embodiment.

FIGS. 4-6 illustrate sensors 202, 212, 222, respectively. The sensors, which may also be referred to as transducers, may be a portion of the wireless devices described herein. Each of the sensors may be configured to measure (e.g., detect) a designated property or characteristic in the environment proximate to the sensor and provide a signal that is representative of the measured property or characteristic. The signal provided by the sensor may be the measurement.

Various types of measurements may be obtained by the sensors. Some non-limiting examples include a capacitance of a liquid, a temperature of a liquid and/or temperatures of certain parts of a machine, a fluid conduction of a liquid, a dielectric constant of a liquid, a dissipation factor of a liquid, an impedance of a liquid, a viscosity of a liquid, or vibrations of a mechanical element. A measurement may be directly obtained (e.g., temperature) by the sensor, or a designated measurement may be obtained after using information provided by the sensor to calculate the designated measurement. For example, the viscosity of the liquid may be calculated based on multiple level measurements obtained by a sensor.

Embodiments may include a single wireless device that is configured to measure and communicate only a single type of measurement (e.g., capacitance). However, in some embodiments, a single wireless device may be configured to measure and communicate multiple types of measurements (e.g., capacitance of the liquid, temperature of the liquid, temperature of the sensor, shock and/or vibration of the gear case, etc.). In such embodiments, the wireless device may have multiple sensors.

The sensor 202 is configured to measure a capacitance of a liquid, such as a lubricant in a tank (e.g., gear case). The sensor 202 is hereinafter referred to as a capacitive level probe 202. For reference, a cross-section 201 of the level probe 202 is also shown in FIG. 4. The level probe 202 extends lengthwise between a leading end 208 and a trailing end 210. The level probe 202 includes an inner or measurement electrode 204 and an outer or reference electrode 206. As shown, a space 205 exists between the inner and outer electrodes 204, 206. A capacitance of the material that exists within the space 205, such as a combination of a liquid and gas, may be measured by the level probe 202. In some embodiments, a wall of the tank that holds the liquid may be used as the reference electrode.

The level probe 202 is configured to be immersed into the liquid (e.g., oil) held by the tank. For example, the leading end 208 may be inserted into the liquid. As the leading end 208 is submerged, the liquid may flow into the space 205 thereby changing a ratio of liquid to gas within the space 205. As such, the measured capacitance changes as the level of the liquid within the space 205 changes. If the liquid is a lubricant, the measured value of capacitance decreases as an amount or level of the liquid decreases. As an amount or level of the liquid increases, the measured value of capacitance also increases.

The level probe 202 may also be configured to determine a quality of the liquid. More specifically, the level probe 202 may detect an amount or percentage of contaminations in the liquid based on capacitance measurements. For example, contaminant detection may be based on a dissipation factor of a dielectric of the liquid. In general, the dissipation factor is a function of an applied frequency, a liquid temperature, a composition of the liquid (e.g., the desired composition of the liquid), and contaminants. The dissipation factor may be substantially independent of the base capacitance or liquid level.

In some cases, movement of the machine may cause a displacement of the liquid which may introduce an error in the measurements. Accordingly, in some embodiments, the level probe 202 is only activated when the machine or component thereof is at rest (e.g., inactive). To this end, an accelerometer or other inertial type sensor may be part of or operably coupled to the wireless device that includes the level probe 202. The accelerometer may determine that the machine is in an inactive or stationary state such that measurements may be obtained by the level probe 202.

As shown in FIG. 5, the sensor 212 includes a body float 214 and a reed switch 216. The body float 214 includes a cavity 218 that is sized and shaped to receive the reed switch 216. The body float 214 is configured to float along the reed switch 216 (e.g., vertically) based on a level of the liquid in the reservoir. The body float 214 includes a permanent magnet 220, and the reed switch 216 includes a magnetically actuated switch or switches (not shown). As the body float 214 moves up and down, the permanent magnet 220 may activate or deactivate the switch (e.g., close or open a circuit, respectively, in the reed switch 216). The activated switch indicates that the body float 214 is at a designated level and, consequently, that the liquid is at a designated level.

As described above, one or more embodiments may also include a sensor that is an accelerometer. FIG. 6 illustrates one such sensor, which is referenced as an accelerometer 222. In some embodiments, the accelerometer 222 is a micro-electro-mechanical system (MEMS) tri-axis accelerometer. The accelerometer 222 may be used for a variety of functions. For example, the accelerometer 222 may be coupled to a mechanical element, such as a tank, and determine whether the mechanical element has remained stationary for a designated amount of time. In some embodiments, other measurements (e.g. liquid level) may be obtained only after it has been determined that the mechanical element has remained stationary for the designated amount of time.

Alternatively or additionally, the accelerometer 222 may be configured to detect vibratory states experienced by the mechanical element. For example, the accelerometer 222 may be configured to obtain numerous shock and vibrations measurements per second in each of x-, y-, and z-axes. For example, the accelerometer 222 may be able to log hundreds or thousands of data points per second in each of the x-, y-, and z-axes.

Figure 7:
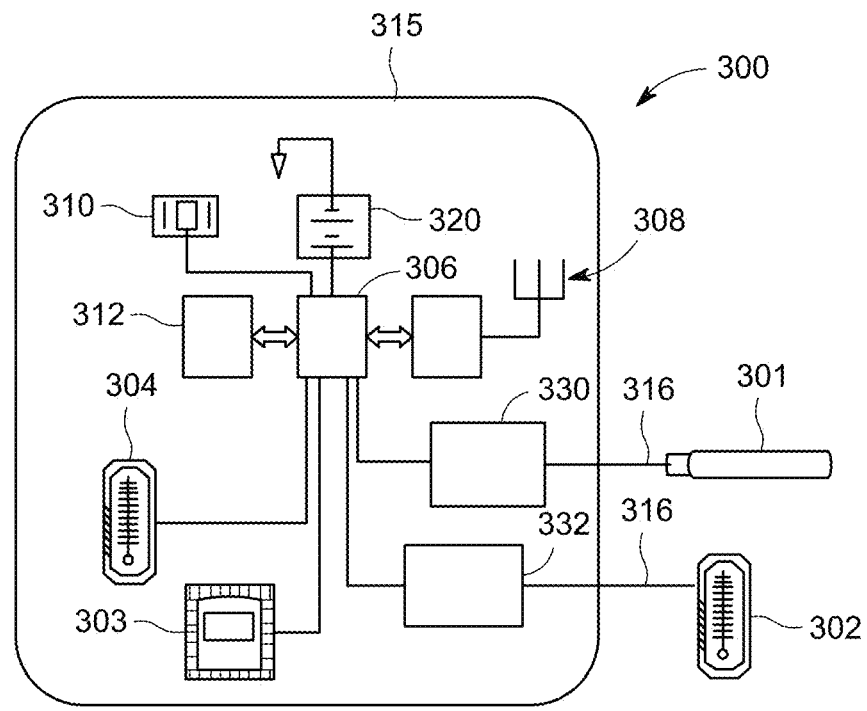
FIG. 7 is a schematic diagram of a wireless device formed in accordance with an embodiment.

FIG. 7 is a schematic diagram of a wireless device 300 formed in accordance with one embodiment. The wireless device 300 includes sensors 301-304, a processing unit 306 (e.g., microprocessor), a transmitter 308, an internal clock 310 (e.g., real-time clock crystal), and a memory 312 (e.g., non-volatile memory). The wireless device 300 has a device body 315, which may include a printed circuit board (PCB) or a die (e.g., semiconductor wafer) in some embodiments. In the illustrated embodiment, the device body 315 includes the sensors 303, 304, the processing unit 306, the transmitter 308, the internal clock 310, and the memory 312. In alternative embodiments, however, the wireless device 300 may have multiple bodies (e.g., multiple dies) that are coupled to each other and/or the components described herein may be separate from the device body 315. The sensors 301 and 302 may be operably coupled to the device body 315 through, for example, wires 316. In other embodiments, the sensors 301, 302 are wirelessly coupled to the device body 315.

The sensor 301 may be a level probe, such as the level probe 202 described with respect to FIG. 4. The sensor 301 is configured to be inserted into a liquid (e.g., lubricant) of a machine. The sensor 302 may be a thermometer that is configured to obtain a temperature of the liquid. The sensor 303 is an accelerometer, such as the accelerometer 222 (FIG. 6), and the sensor 304 is another thermometer that is configured to determine a temperature of the device body 315 of the wireless device 300. Each of the sensors 301-304 is communicatively coupled to the processing unit 306 and configured to communicate signals to the processing unit 306. The signals may be representative of a property or characteristic detected by the sensor.

The processing unit 306 may be configured to store or log data (e.g., data based on the signals obtained from the sensors) in the memory 312. In some embodiments, the processing unit 306 is configured to query the sensors 301-304 to request measurements from the sensors 301-304. The queries may occur at predetermined times or when a designated event occurs. For example, the queries may occur once an hour as determined by the internal clock 310 until, for example, the wireless device 300 is interrogated by a reader (not shown). At such an event, the processing unit 306 may query the sensors 301-304 for numerous data points. For example, the data points may be provided almost continuously after interrogation. The processing unit 306 may also receive data from the memory 312. The data received from the sensors 301-304 and/or the memory 312 may be transformed into data signals that are communicated by the transmitter 308 to the reader.

The wireless device 300 may be characterized as an active or semi-passive device. For example, the wireless device 300 may include a power source 320, such as a battery (e.g., lithium thionyl chloride battery) and/or kinetic energy harvesting device. The wireless device 300 may utilize the power source 320 to increase the transmission range of the transmitter 308. In such embodiments, the reader may be located tens or hundreds of meters away from the wireless device 300. In addition to the transmitter 308, the power source 320 may be used to supply power to other components of the wireless device 300, such as the sensors 301-304 or the processing unit 306.

Figure 8:
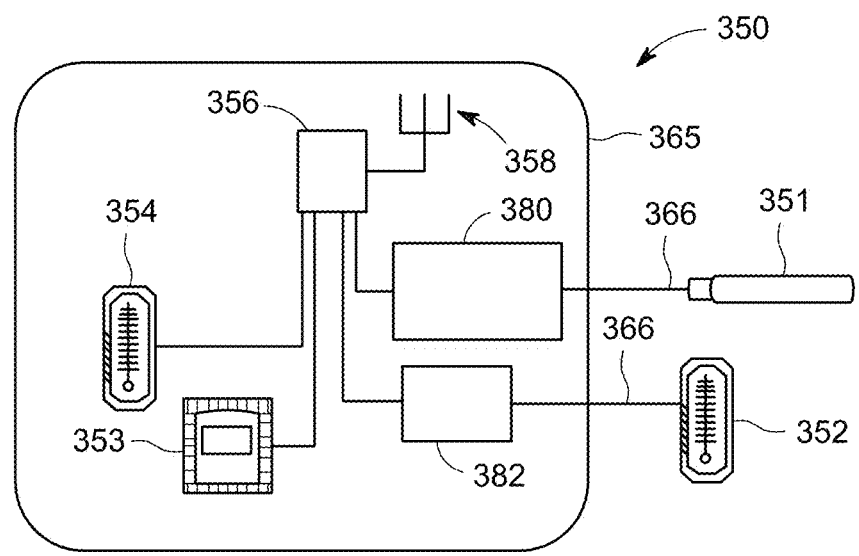
FIG. 8 is a schematic diagram of a wireless device formed in accordance with an embodiment.

FIG. 8 is a schematic diagram of a wireless device 350 formed in accordance with one embodiment. The wireless device 350 may be a passive device such that the wireless device 350 is powered by inductive or backscatter coupling with the reader (or some other non-internal power source). As shown, the wireless device 350 includes sensors 351-354, a processing unit 356, and a transmitter 358. The wireless device 300 has a device body 365 that includes, in the illustrated embodiment, the sensors 353, 354, the processing unit 356, and the transmitter 358. The device body 365 may be formed by integrated circuit technology. For example, the device body 365 may include one or more printed circuit boards (PCBs). The sensors 351 and 352 may be operably coupled to the device body 365 through, for example, wires 366. Similar to the wireless device 300 (FIG. 7), the sensors 351-354 may be a level probe, external thermometer, an accelerometer, and an internal thermometer, respectively.

In some embodiments, the processing unit 356 executes fewer calculations or conversions of the signals from the sensors 351-354 than the processing unit 306 (FIG. 7). For example, the processing unit 356 may be an ADC that converts the analog signals from the sensors 351-354 to digital signals. The digital signals may be the data signals that are then transmitted by the transmitter 358. In the illustrated embodiment, the processing unit 356 may only query the sensors 351-354 after being interrogated by a reader (not shown). More specifically, the interrogation signals from the reader may power the processing unit 356 to query the sensors 351-354 and transmit the data signals.

Figures 9, 10:
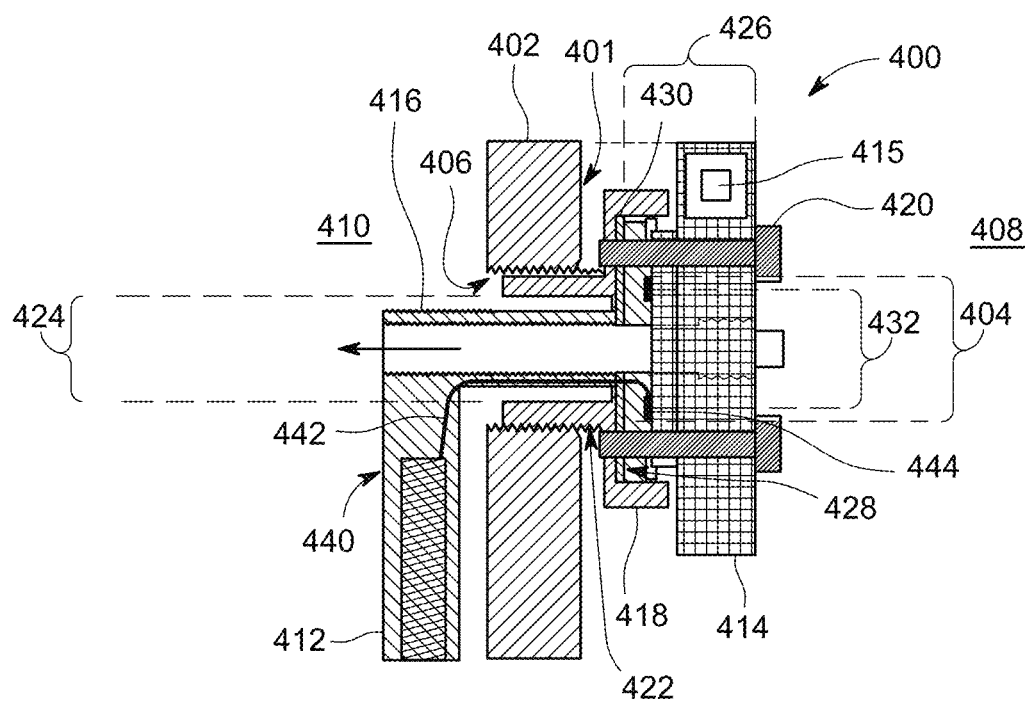
FIG. 9 is a cross-section of a portion of a wireless device utilizing the sensor of FIG. 4 in accordance with an embodiment.
FIG. 10 is a cross-section of a portion of a wireless device utilizing the sensor of FIG. 4 in accordance with an embodiment.

FIG. 9 is a cross-section of a portion of a wireless device 400 attached to a wall 402 of a tank 401. The tank 401 may be part of a machine, such as a locomotive or other machines described herein. The tank 401 is configured to have a reservoir 410 for holding a liquid (not shown), such as a lubricant. The reservoir 410 is accessed through a fill port 404 of the wall 402 that is defined by interior threads 406 of the wall 402 as shown in FIG. 9. The fill port 404 provides access from an exterior 408 of the tank 401 to the reservoir 410.

As shown, the wireless device 400 includes a sensor 412, a device body 414, and an intermediate cable portion 416 that joins the sensor 412 and the device body 414. The wireless device 400 also includes a coupling component 418 that is configured to be secured to the device body 414 through, for example, fasteners 420 and attached to the wall 402. In the illustrated embodiment, the coupling component 418 includes threads 422 that complement and are configured to rotatably engage the threads 406 of the wall 402. However, in other embodiments, different methods of attaching the coupling component 418 to the tank may be used, such as latches, interference fits (e.g., plugs), and/or adhesives.

To assemble the wireless device 400, the coupling component 418 may be rotatably engaged to the wall 402. The sensor 412 and the cable portion 416 may be inserted through an opening 424 of the coupling component 418 and the fill port 404. As shown, the coupling component 418 has a mating face 428 that faces in a direction away from the wall 402. The cable portion 416 has a mating end 426 that is located in the exterior 408 of the tank 401 and may be pressed toward the mating face 428 with a gasket 430 located therebetween. The device body 414 has a cable opening 432 that receives an end of the cable portion 416. The device body 414 may be secured to the cable portion 416 and the coupling component 418 using the fasteners 420. As shown, the cable portion 416 includes a fill channel 436 that permits access to the reservoir 410. During operation, the fill channel 436 may be closed with a plug 438 at the mating end 426 of the cable portion 416.

The sensor 412 may be similar or identical to the level probe 202 described with respect to FIG. 4. For example, a trailing end 440 of the sensor 412 is shown in FIG. 9. The trailing end 440 is coupled to wires 442 that communicatively couple the sensor 412 to the device body 414. In other embodiments, the sensor 462 may be similar or identical to the sensor 212 (FIG. 5). The cable portion 416 is configured to surround and protect the wires 442 from the surrounding environment. As shown, the wires 442 terminate at a contact ring 444 along the device body 414. The sensor 412 is configured to transmit signals to the device body 414 through the wires 442 and the contact ring 444. The device body 414 is configured to process and transmit data signals that represent measurements obtained by the sensor 412. The device body 414 may include an integrated circuit unit 415. Although not shown, the integrated circuit unit 415 of the device body 414 may have a processing unit, power source, internal clock, additional sensors, and/or a transmitter, such as those described above. In some embodiments, the integrated circuit component 415 is formed as an RFID unit.

FIG. 10 is a cross-section of a portion of a wireless device 450, which is also configured to be coupled to a wall 452 of a tank 451. The wireless device 450 may include similar features as the wireless device 400 (FIG. 9). For example, the wireless device 450 includes a sensor 462, a device body 464, and an intermediate cable portion 466 that joins the sensor 462 and the device body 464. The wireless device 450 also includes a coupling component 468 that is configured to be secured directly to the device body 464 and the cable portion 466 through fasteners 470. In the illustrated embodiment, the coupling component 468 is rotatably engaged to the wall 452 in a similar manner as the coupling component 418 (FIG. 9). However, other methods of attaching the coupling component 468 to the wall may be used.

To assemble the wireless device 450, the coupling component 468 may be rotatably engaged to the wall 452. The sensor 462 and the cable portion 466 may be inserted through the coupling component 416 and a fill port 454 of the wall 452. The device body 464 may be encased within a mating end 476 of the cable portion 466. As shown, the coupling component 468 has a mating face 478 that faces in a direction away from the wall 452. Accordingly, the cable portion 466 and the device body 464 may be secured to the coupling component 468 using the fasteners 470. A cover body 480 may then be positioned over the cable portion 466 to hold the device body 464 between the cover body 480 and the coupling component 468. Unlike the wireless device 400, the cable portion 466 does not include a fill channel that permits access to the reservoir.

The sensor 462 may be similar or identical to the level probe 202 described with respect to FIG. 4. For example, a trailing end 490 of the sensor 462 is shown in FIG. 10. The trailing end 490 is coupled to wires 492 that communicatively couple the sensor 462 to the device body 464. In other embodiments, the sensor 462 may be similar or identical to the sensor 212 (FIG. 5). As shown, the wires 492 terminate at contacts 494, 495 that are coupled to the device body 464. The device body 464 may include an integrated circuit component 465, which, in the illustrated embodiment, is a RFID unit. The sensor 462 is configured to transmit signals to the integrated circuit component 465 through the wires 492. Like the integrated circuit component 415, the integrated circuit component 465 is configured to process and transmit data signals that represent measurements obtained by the sensor 462. The integrated circuit component 465 may include a processing unit, power source, internal clock, additional sensors, and/or a transmitter, such as those described above.

FIG. 11 is a cross-section of a portion of a wireless device 500. The wireless device 500 may be similar to the wireless device 400 (FIG. 9) and the wireless device 450 (FIG. 10).

However, as shown in FIG. 11, the wireless device 500 utilizes a sensor 502 that may be similar to or identical to the sensor 212 (FIG. 5). The wireless device 500 also includes a coupling component 504 that is configured to attach to a wall 506 of a tank 508, which is a gear case in the illustrated embodiment. The coupling component 504 may be similar to the coupling components described above. For example, the coupling component 504 may rotatably engage the wall 506.

Also shown, the wireless device 500 includes a device body 530 that is operably coupled to the sensor 502 through a base support 510 and an intermediate beam 512. The base support 510 is disposed within an opening 514 of the coupling component 504. The beam 512 extends between and joins the sensor 502 and the base support 510. The beam 512 may be fabricated from, for example, stainless steel and is configured to provide a passageway 516 for wires 518 that communicatively couple the device body 530 and the sensor 502.

The base support 510 includes a mating face 520 that faces away from the tank 508. The mating face 520 has contacts 524, 525 thereon. The contact 524 may be a contact pad, and the contact 525 may be a ring contact that extends around the contact pad. A device body 530 is configured to be rotatably engaged to the coupling component 504. The device body 530 includes a mounting surface 532 that faces the mating face 520 and has corresponding contacts that are configured to engage the contacts 524, 525. More specifically, when the device body 530 is rotated to engage the coupling component 504, the mounting surface 532 of the device body 530 may advance toward the mating face 520 so that the contacts of the device body 530 press against and engage the contacts 524, 525.

Accordingly, the device body 530 may be communicatively coupled to the sensor 502. Similar to the device bodies described above, the device body 530 may include an integrated circuit component 515 having a processing unit and a transmitter (not shown). Optionally, the integrated circuit component 515 may also include a memory, an internal clock, and one or more other sensors. The integrated circuit component 515 may transform the signals from the sensor 502 (or memory or other sensors) into data signals. The data signals may then be transmitted to a reader (not shown). In some embodiments, the integrated circuit component 515 is formed as an RFID unit.

FIG. 12 is a cross-section and FIG. 13 is a front view, respectively, of a portion of a wireless device 550. The wireless device 550 may include a sensor (not shown) and a device body 552 that are communicatively coupled through wires 554. The sensor may be similar to the sensor 202 (FIG. 4) or the sensor 212 (FIG. 5). The device body 552 is secured to a faceplate 556 that is coupled to an exterior surface of a tank 560 (FIG. 13). FIGS. 12 and 13 illustrate an embodiment in which no electrical contacts are required along the device body 552 to electrically join the sensor. Instead, wires 554 (FIG. 12) from the sensor may extend through potting 562 that mechanically couples the sensor to the tank 560. Like the wireless device 400 (FIG. 9), the wireless device 550 may permit access to a fill port 566 through a plug 568. Although not shown, the device body 552 may include an integrated circuit component, such as those described above, that processes data signals and transmits data signals. The integrated circuit component may be an RFID unit that is directly coupled to one of the wires 554.

Figure 14:
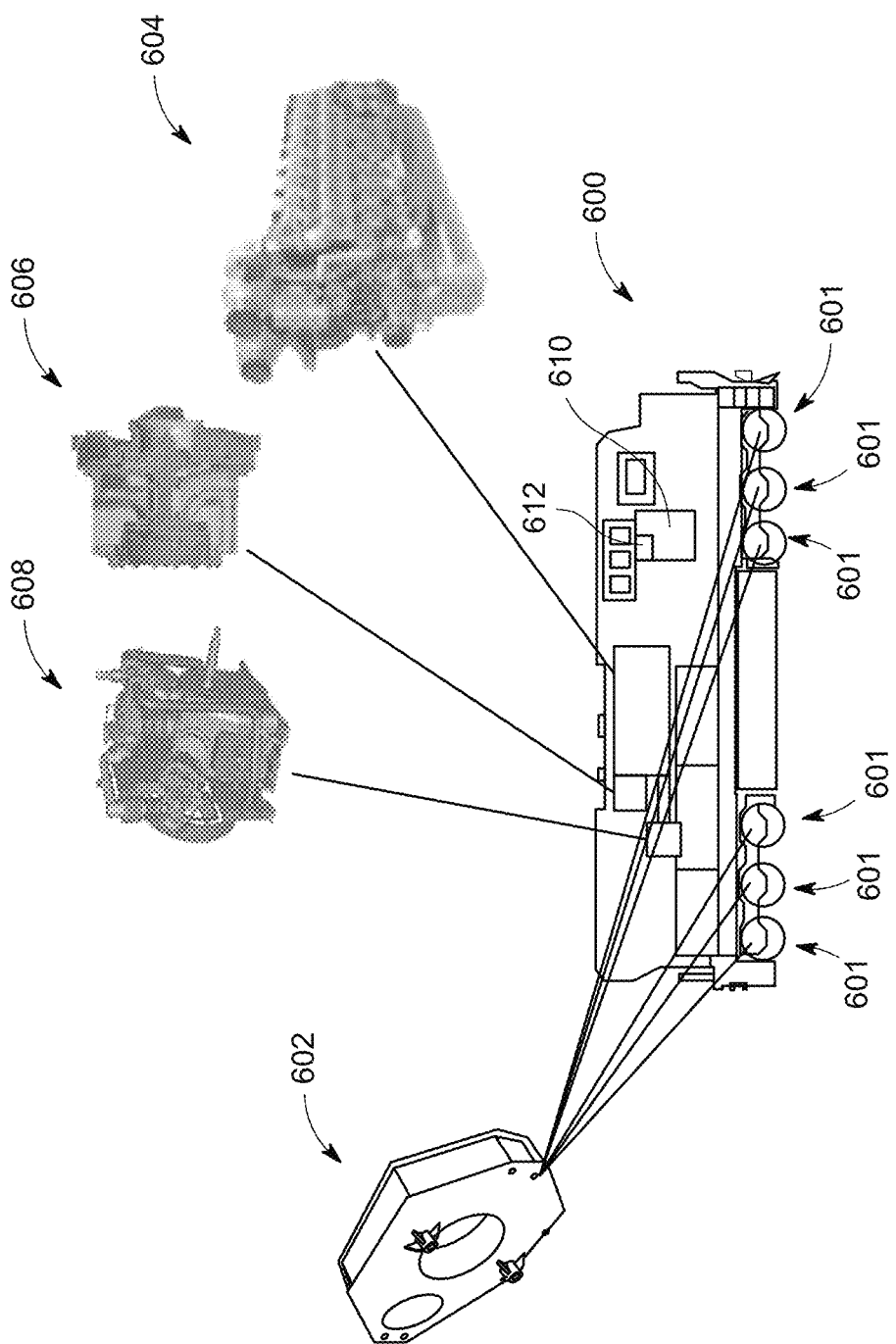
FIG. 14 is a schematic view of a locomotive and illustrates a plurality of components of the locomotive in accordance with an embodiment.

FIG. 14 is a schematic view of a locomotive 600 and illustrates a plurality of components of the locomotive 600 that may include one or more wireless devices, such as the wireless devices described herein. For example, the locomotive 600 may include a plurality of drive trains 601 that each has a gear case 602. The locomotive 600 may also include an engine 604, a turbo-charger 606 operably coupled to the engine 604, and an air compressor 608. Each of the components may have one or more of the wireless devices described herein operably coupled thereto. For example, the gear cases 602 and the engine 604 may have at least one of the wireless devices 202, 212, 222, 400, 450, 500, or 550 described above. In particular, each of the gear cases 602 and the engine 604 may have a reservoir that includes a liquid lubricant. The turbo-charger 606 and the air compressor 608 may use, for example, an accelerometer similar to the wireless device 222.

As shown, the locomotive 600 may also include an on-board control system 610. The control system 610 can control the tractive efforts and/or braking efforts of the locomotive 600 and, optionally, other locomotives that are directly or indirectly coupled to the locomotive 600. Operations of the control system 610 may be based on inputs received from an operator of the locomotive and/or remote inputs from, for example, a control tower, a dispatch facility, or the like. In addition, the control system 610 may receive inputs from various components of the locomotive 600. In some cases, the inputs may be data signals received through wireless communication. For example, the wireless devices of the gear cases 602, the engine 604, the turbo-charger 606, and the air compressor 608 may be configured to wirelessly communicate data signals to the control system 610. The control system 610 may include a reader 612 for receiving the wireless data signals. The control system 610 may also include a signal-processing module and a planning module that are similar to the signal-processing and planning modules 120, 122 described in FIG. 1. The planning module may generate operating plans for the locomotive 600 based on the inputs received.

Figure 15:
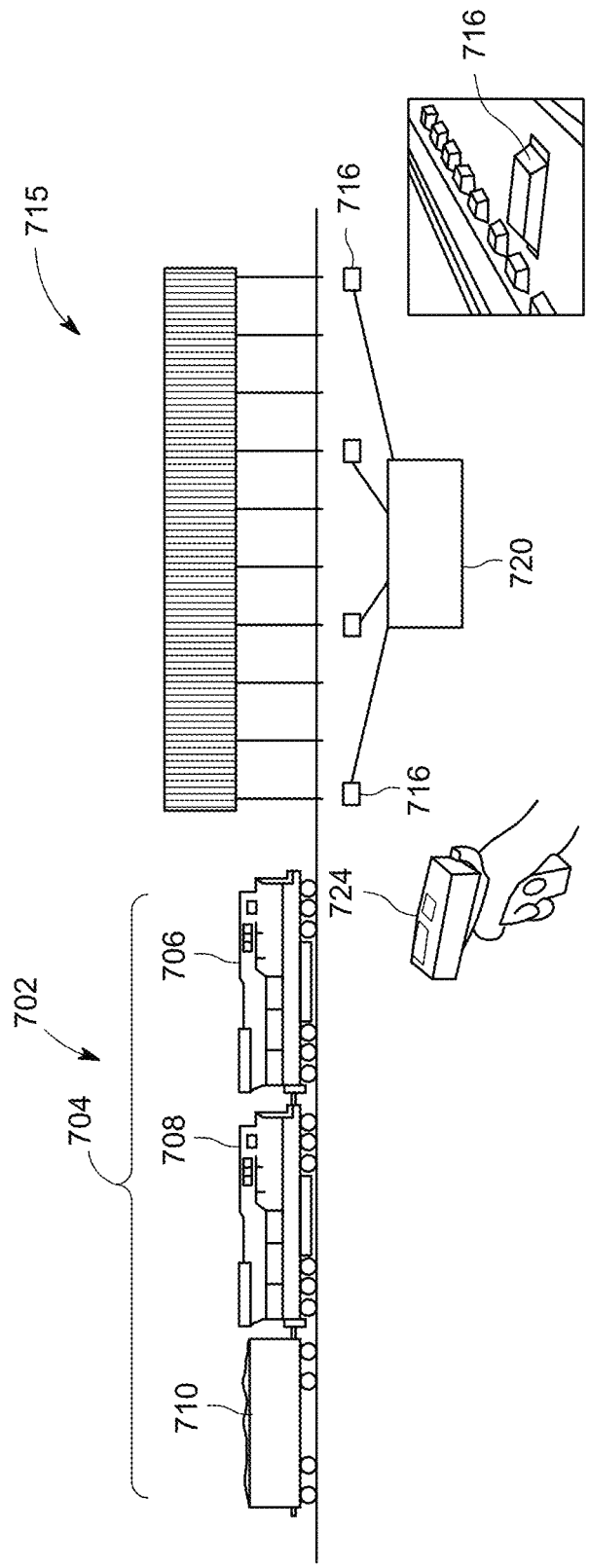
FIG. 15 illustrates a system in accordance with an embodiment for obtaining data signals from one or more wireless devices.
Figure 16:
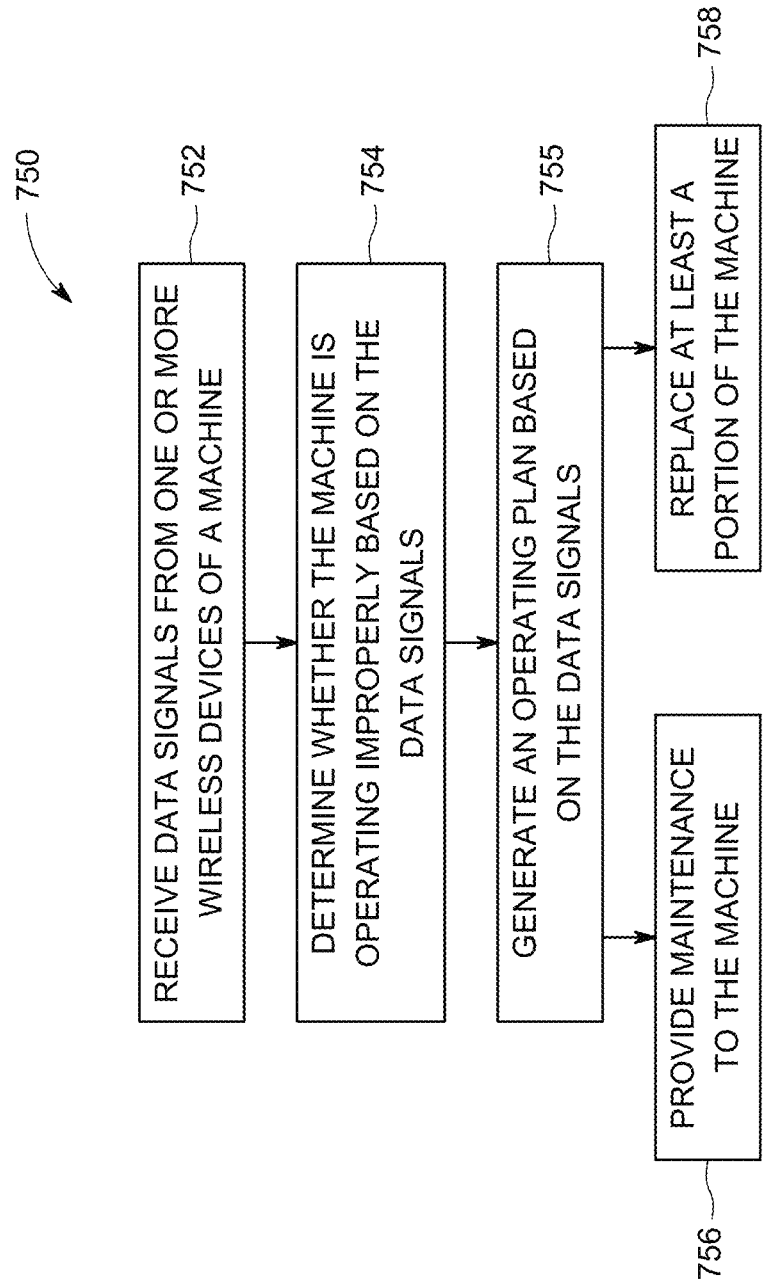
FIG. 16 is a flowchart illustrating a method in accordance with an embodiment.

FIG. 15 illustrates a system 700 in accordance with one embodiment for obtaining data signals from one or more wireless devices. FIG. 16 illustrates a flowchart of a method 750 that may be executed or performed by the system 700. In some embodiments, the locomotive 600 (FIG. 14) may also execute or perform the method 750. The system 700 and the method 750 may employ structures or aspects of various embodiments discussed herein. In some embodiments, certain steps of the method 750 may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Likewise, the system 700 is not required to include each and every feature of each and every embodiment described herein.

With respect to FIG. 15, the system 700 includes a vehicle system 702 (e.g., train) including a locomotive consist 704. The locomotive consist 704 may include at least one locomotive that is linked (directly or indirectly) to one or more rail cars. For example, FIG. 15 shows the locomotive consist 704 including first and second locomotives 706, 708 and a rail car 710. In other embodiments, the vehicle system 702 may include more rail cars 710. Each of the locomotives 706 and 708 may include a plurality of components that are each monitored by one or more wireless devices. For example, each of the locomotives 706, 708 may include an engine, a turbo-charger, an air compressor, and a plurality of gear cases, such as those described herein.

As shown in FIG. 15, the vehicle system 702 is approaching a designated reading location 715. The reading location 715 is a maintenance facility in the illustrated embodiment. However, the reading location 715 may be a variety of other locations that are capable of receiving wireless data signals from the locomotives. For example, the reading location 715 may be a depot, fuel station, wayside location, rail yard entry point or exit point, designated sections of the track(s), and the like. The reading location 715 includes a plurality of readers 716. Each of the readers 716 is communicatively coupled (e.g., wirelessly or through communication wires) to a control system 720. Alternatively or additionally, a handheld reader 724 may be carried by an individual and used to receive the data signals. The reader 724 may also communicate data signals with the control system 720.

The control system 720 may include a signal-processing module and a planning module, such as the signal-processing and planning modules 120, 122 described in FIG. 1. For example, the control system 720 may generate operating plans that include instructions for operating the vehicle system 702 and other similar vehicle systems.

The method 750 may include receiving (at 752) data signals from one or more of the wireless devices of a machine. In the illustrated embodiment, the machine is the vehicle system 702 or one of the locomotives 704, 706. However, embodiments described herein are not necessarily limited to locomotives. The machine may have one or components with moving mechanical elements or parts. For example, the machine may have a drive train, engine, air compressor, and/or turbo-charger. The data signals may be representative of a measurement of an operative condition of the component. By way of example the measurement may be at least one of a vibration measurement, a capacitance of a liquid, a temperature of a liquid, a fluid conduction of a liquid, a dielectric constant of a liquid, an impedance of a liquid, or a viscosity of a liquid. In particular embodiments, the measurement is representative of a vibratory state of a gear case or of a liquid condition of a lubricant held in the gear case.

The receiving operation (at 752) may include receiving the data signals at one or more fixed readers having stationary positions. For example, the readers 716 may have fixed positions with respect to tracks 730. The readers 716 may be located at designated distance from the tracks 730 so that the readers 716 are capable of receiving the data signals. The receiving operation (at 752) may also include receiving the data signals through one or more movable readers, such as the handheld reader 724.

In an alternative embodiment, as described above, the receiving operation (at 752) may occur with an on-board control system, such as the control system 610 (FIG. 14).

The method 750 also included determining (at 754), based on the data signals, whether the component of the machine is operating improperly. For example, the control system 720 may analyze the data signals and, optionally, other inputs to determine whether the component is operating sufficiently. If the component is operating improperly, the method 750 also includes generating (at 755) an operating plan that is based on the data signals. The operating plan may be a new (or revised) operating plan that is configured to replace a currently-implemented operating plan. The method 750 may also include at least one of providing maintenance (at 756) to the component or replacing (at 758) an element of the component.

In an embodiment, a system (e.g., a monitoring system) is provided that includes a sensor configured to be disposed within a reservoir of a machine having moving parts that are lubricated by a liquid in the reservoir. The sensor is configured to obtain a measurement of the liquid that is representative of at least one of a quantity or quality of the liquid in the reservoir. The system may also include a device body operably coupled to the sensor. The device body has a processing unit that is operably coupled to the sensor and configured to generate first data signals representative of the measurement of the liquid. The device body also includes a transmitter that is configured to wirelessly communicate the first data signals to a remote reader.

In one aspect, the transmitter is configured to be energized by the reader when the reader interrogates the transmitter.

In one aspect, the system includes a power source that is configured to supply power to the transmitter for transmitting the data signals. The power source may include, for example, a battery and/or energy harvesting device.

In one aspect, the sensor is configured to be at least partially submerged in the liquid.

In one aspect, the measurement is at least one of a capacitance of the liquid, a temperature of the liquid, a fluid conduction of the liquid, a dielectric constant of the liquid, an impedance of the liquid, or a viscosity of the liquid.

In one aspect, the device body is configured to be affixed to a wall of the machine in which the wall at least partially defines the reservoir.

In one aspect, the sensor and the device body collectively form a first wireless device. The system may also include a second wireless device that is configured to obtain and wirelessly communicate second data signals that are representative of a measurement of a different reservoir.

In one aspect, the sensor is configured to be disposed in a gear case of a locomotive, the gear case having the reservoir.

In one aspect, the transmitter is included in a radio-frequency identification (RFID) element.

In one aspect, the sensor, the processing unit, and the transmitter collectively form a first wireless device. The system may also include a second wireless device that is configured to obtain and wirelessly transmit data signals that are representative of a measurement of a different reservoir. The system may include a signal-processing module. The signal-processing module may be configured to determine, based on the data signals, whether the machine is operating improperly by comparing the data signals of the first wireless device to the data signals of the second wireless device.

In one aspect, the data signals are configured to be transmitted to a handheld reader. In another aspect, the data signals are configured to be transmitted to a fixed reader located along a railway track. In yet another aspect, the data signals are configured to be transmitted to an on-board reader located on a locomotive.

In one aspect, the sensor includes a multi-conductor capacitive sensor configured to detect a capacitance of a fluid. The fluid may function as a dielectric, wherein a level of the fluid affects the capacitance detected. In another aspect, the sensor includes a body float and a position transducer configured to detect a position of the body float. The position transducer may include, for example, a reed switch.

In an embodiment, a system (e.g., a monitoring system) is provided that includes a sensor that is configured to be engaged to a mechanical element of a drive train to obtain a measurement of a vibratory state of the mechanical element. The measurement is representative of an operative condition of the drive train. The system includes a device body that has a processing unit operably coupled to the sensor. The processing unit is configured to generate first data signals representative of the measurement. The device body also includes a transmitter that is configured to wirelessly communicate the first data signals to a remote reader.

In one aspect, the system includes a power source configured to supply power to the transmitter for transmitting the data signals.

In one aspect, the system includes a memory. The memory is configured to log a plurality of the measurements obtained at different times. The transmitter is configured to transmit data signals that include the measurements.

In one aspect, the sensor, the processing unit, and the transmitter collectively form a first wireless device. The system may include a second wireless device configured to obtain and wirelessly transmit data signals that are based on a measurement of a different drive train.

In one aspect, the device body includes a radio-frequency identification (RFID) unit. The RFID unit may have the processing unit and the transmitter.

In an embodiment, a method (e.g., a method for monitoring an operative condition of a machine) includes receiving data signals from a wireless device of a machine having a drive train. The wireless device includes a device body directly coupled to the drive train. The device body includes a transmitter for wirelessly transmitting the data signals. The data signals may be based on a measurement of an operative condition of the drive train. The method also includes, responsive to determining that the drive train is operating improperly, generating signals to schedule at least one of maintenance of the drive train or replacement of an element of the drive train.

In one aspect, the measurement is representative of vibratory state of a gear case or a liquid condition of a lubricant held in the gear case.

In one aspect, the measurement is at least one of a vibration measurement of a gear case, a capacitance of a lubricant stored by the gear case, a temperature of the lubricant, a fluid conduction of the lubricant, a dielectric constant of the lubricant, impedance of the lubricant, or a viscosity of the lubricant.

In one aspect, the data signals are received from a plurality of wireless devices. The data signals are based on a common type of measurement.

In one aspect, the data signals are received at a handheld reader.

In one aspect, the machine is a locomotive and the data signals are received at a fixed reader located along a railway track.

In one aspect, the machine is a locomotive and the data signals are received at a reader located on-board the locomotive.

In one aspect, the method also includes operating the machine according to a first operating plan and generating a second operating plan that is based on the operative condition.

In an embodiment, a system (e.g., a monitoring system) includes a signal-processing module that is configured to receive data signals from a wireless device of a machine having a drive train. The data signals are based on a measurement of an operative condition of the drive train. The signal-processing module is configured to determine, based on the data signals, whether the drive train is operating improperly. Optionally, the system also includes a planning module that is configured to generate an operating plan that is based on the operative condition.

In another embodiment, a system (e.g., wireless liquid monitoring system) comprises a sensor, a processing unit, and a transmitter. The sensor is configured to be disposed within a reservoir of a machine having moving parts that are lubricated by a liquid in the reservoir. The sensor is configured to obtain a measurement of the liquid that is representative of at least one of a quantity or quality of the liquid in the reservoir. The processing unit is operably coupled to the sensor and configured to generate first data signals representative of the measurement of the liquid. The transmitter is operably coupled to the processing unit and configured to wirelessly communicate the first data signals to a remote reader.

In another embodiment of the system, alternatively or additionally, the transmitter is an RFID unit, which may be, for example, similar to an RFID tag, chip, card, or label.

In another embodiment of the system, alternatively or additionally, the system is configured to be disposed in the machine (and when installed is actually disposed in the machine), which comprises a vehicle or other powered system comprising the reservoir, the moving parts, and one or more computers or other controller-based units (e.g., a vehicle controller) other than the processing unit. The system may not be physically electrically connected (e.g., not connected by wires or other conductors) to any of the one or more computers or other controller-based units in the machine. Thus, the first data signals may only be wirelessly transmitted from the system to the reader or elsewhere, and are not transmitted via wire/cables or other physical electrical connections.

In another embodiment of the system, alternatively or additionally, the processing unit and transmitter are co-located proximate to one another (e.g., at least partially integrated onto a common circuit board, positioned within a common box/housing that is positioned within the machine—that is, the common box/housing is not coextensive with the outer body/structure of the machine, but is located within the outer body/structure—and/or some or all of the components of the processing unit and transmitter are located within 10 cm of each other, within 5 cm of each other, etc., for example), and/or at least portions of the processing unit and transmitter are directly connected to a wall of the reservoir (e.g., a wall that bears a pressure of and/or contacts the liquid in the reservoir) and/or to a structure immediately connected to such a wall (e.g., support structure of the reservoir, gear case, or the like).

In another embodiment of the system, alternatively or additionally, the transmitter is configured to wirelessly communicate the first data signals to the remote reader that comprises: a remote reader located within the machine (e.g., if the machine is a vehicle, the remote reader is located with the vehicle); a remote reader located on a wayside of a route of the machine, the machine comprising a vehicle; a portable (handheld, or otherwise able to be carried by a human operator) remote reader.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system," "module," or "controller" may include hardware and/or software that operate(s) to perform one or more functions. For example, a system, module, or controller may include a computer processor or other logic-based device that performs operations based on instructions stored on a tangible and non-transitory computer readable storage medium, such as a computer memory. Alternatively, a system, module, or controller may include a hard-wired device that performs operations based on hard-wired logic of the device. The systems, modules, and controllers shown in the Figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
a sensor sized to be within a reservoir of a machine having moving parts that are lubricated by a liquid in the reservoir, the sensor configured to obtain a measurement of the liquid that is representative of one or more of a quantity or quality of the liquid in the reservoir; and
a device body operably coupled with the sensor, the device body including a processing unit and a transponder, the transponder configured to wirelessly receive an interrogation signal from a remote reader that includes electric energy that energizes the processing unit to generate a data signal representative of the measurement of the liquid obtained by the sensor, the electric energy of the interrogation signal additionally energizing the transponder to wirelessly communicate the data signal to the remote reader;
the device body further including an accelerometer operably coupled to the processing unit and configured to obtain a vibration measurement of the reservoir, the processing unit configured to generate the data signal representative of the measurement of the liquid for communication by the transponder during the stationary state of the machine based on the vibration measurement.

2. The system of claim 1, wherein the sensor is configured to obtain the measurement of the liquid responsive to receiving a query from the processing unit requesting the measurement, the processing unit configured to communicate the query to the sensor responsive to receiving the interrogation signal.

3. The system of claim 1, further comprising a power source configured to supply power to the transponder for communicating the data signal.

4. The system of claim 1, wherein the sensor is configured to be at least partially submerged in the liquid.

5. The system of claim 1, wherein the measurement is at least one of a fluid level, a temperature of the liquid or nearby components, a fluid conduction of the liquid, a dielectric constant of the liquid, an impedance of the liquid, or a viscosity of the liquid.

6. The system of claim 1, wherein the machine is a vehicle and the reservoir is in a gear case of the vehicle.

7. The system of claim 1, wherein the device body is configured to be affixed to a wall of the machine, the wall at least partially defining the reservoir.

8. The system of claim 1, wherein the remote reader comprises at least one of a handheld reader, a fixed reader located along a route, or an on-board reader located on a vehicle.

9. The system of claim 1, wherein the sensor comprises a multi-conductor capacitive sensor configured to detect a capacitance of the liquid with the liquid functioning as a dielectric, wherein a level of the liquid affects the capacitance that is detected.

10. The system of claim 1, wherein the sensor comprises a body float and a position transducer configured to detect a position of the body float.

11. The system of claim 1, wherein the sensor is configured to communicate data representative of the measurement of the liquid to the processing unit as an analog signal, the processing unit including an analog-to-digital converter that converts the analog signal to a digital signal to generate the data signal.

12. The system of claim 1, wherein the processing unit is configured to determine that the machine is in an active state based on the vibration measurement from the accelerometer indicating greater than the threshold amount of vibration of the wall, the processing unit configured to not generate the data signal representative of the measurement of the liquid during the active state of the machine.

13. The system of claim 1, wherein the sensor is a capacitive sensor configured to be disposed in contact with the liquid to obtain a capacitance measurement of the liquid, the system further comprising a temperature sensor operably coupled to the device body and disposed in contact with the liquid to obtain a temperature measurement of the liquid, the device body mounted to a wall of the reservoir and spaced apart from the liquid in the reservoir, the capacitive sensor and the temperature sensor operably coupled to the device body via corresponding wires.

14. The system of claim 1, further comprising a cable portion extending between the sensor and the device body, the cable portion configured to extend through a port of a wall of the machine, wherein the wall at least partially defines the reservoir, the cable portion extending between a first end outside of the reservoir that is secured to the device body and a second end inside the reservoir that is secured to the sensor, the cable portion housing one or more wires extending between the sensor and the device body to electrically connect the sensor to the device body.

15. The system of claim 14, wherein the cable portion defines a fill channel that provides fluid access to the reservoir from outside of the wall.

16. The system of claim 1, wherein the device body includes an activator coupled to the processing unit, the activator configured to provide a stimulus that causes a response; wherein the measurement of the liquid obtained is based on the response.

17. A system comprising:
a sensor sized to be disposed within a reservoir of a machine having moving parts that are lubricated by a liquid in the reservoir, the sensor configured to obtain a measurement of the liquid that is representative of at least one of a quantity or quality of the liquid in the reservoir; and
a device body operably coupled to the sensor, the device body including a processing unit and a transmitter, the processing unit configured to communicate a query to the sensor requesting the sensor to obtain the measurement of the liquid responsive to receiving an interrogation signal from a remote reader, the processing unit further configured to generate a data signal representative of the measurement of the liquid obtained by the sensor, the transmitter configured to wirelessly communicate the data signal to the remote reader;
the device body further including an accelerometer operably coupled to the processing unit and configured to obtain a vibration measurement of the reservoir, the processing unit configured to generate the data signal representative of the measurement of the liquid for communication by the transmitter during the stationary state of the machine based on the vibration measurement.

18. The system of claim 17, wherein the transmitter is configured to use electric energy of the interrogation signal to energize the transmitter to wirelessly communicate the data signal to the remote reader.

* * * * *